US009625387B2

(12) United States Patent
Demos et al.

(10) Patent No.: US 9,625,387 B2
(45) Date of Patent: *Apr. 18, 2017

(54) SYSTEM AND METHOD FOR CONTROLLING DEPTH OF IMAGING IN TISSUES USING FLUORESCENCE MICROSCOPY UNDER ULTRAVIOLET EXCITATION FOLLOWING STAINING WITH FLUORESCING AGENTS

(71) Applicants: Lawrence Livermore National Security, LLC, Livermore, CA (US); THE REGENTS OF THE UNIVERSITY OF CALIFORNIA, Oakland, CA (US)

(72) Inventors: Stavros Demos, Livermore, CA (US); Richard Levenson, Davis, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 120 days.

This patent is subject to a terminal disclaimer.

(21) Appl. No.: 14/487,997

(22) Filed: Sep. 16, 2014

(65) Prior Publication Data
US 2016/0077007 A1    Mar. 17, 2016

(51) Int. Cl.
*G06K 9/00* (2006.01)
*G01N 21/64* (2006.01)
*A61B 5/00* (2006.01)

(52) U.S. Cl.
CPC ..... *G01N 21/6458* (2013.01); *G01N 21/6428* (2013.01); *G01N 21/6445* (2013.01);
(Continued)

(58) Field of Classification Search
CPC ........... G06K 9/00127; G06K 9/00134; G01N 21/6458; G01N 21/6428; G01N 21/6445;
(Continued)

(56) References Cited

U.S. PATENT DOCUMENTS

| | | | |
|---|---|---|---|
| 6,208,749 B1 * | 3/2001 | Gutkowicz-Krusin | A61B 5/442 356/303 |
| 2005/0065440 A1 * | 3/2005 | Levenson | A61B 5/0059 600/476 |

(Continued)

FOREIGN PATENT DOCUMENTS

WO    2013093843 A1    6/2013

OTHER PUBLICATIONS

Lin, Bevin, et al. "Real-time microscopic imaging of esophageal epithelial disease with autofluorescence under ultraviolet excitation." Optics express 17.15 (2009): 12502-12509.*

(Continued)

*Primary Examiner* — Kim Vu
*Assistant Examiner* — Jonathan S Lee
(74) *Attorney, Agent, or Firm* — Harness & Dickey LLP

(57) ABSTRACT

The present disclosure relates to a method for analyzing tissue specimens. In one implementation the method involves obtaining a tissue sample and exposing the sample to one or more fluorophores as contrast agents to enhance contrast of subcellular compartments of the tissue sample. The tissue sample is illuminated by an ultraviolet (UV) light having a wavelength between about 200 nm to about 400 nm, with the wavelength being selected to result in penetration to only a specified depth below a surface of the tissue sample. Inter-image operations between images acquired under different imaging parameters allow for improvement of the image quality via removal of unwanted image components. A microscope may be used to image the tissue sample and provide the image to an image acquisition system that makes use of a camera. The image acquisition system may create a corresponding image that is transmitted to a display system for processing and display.

21 Claims, 5 Drawing Sheets

(52) U.S. Cl.
CPC ........ *G01N 21/6486* (2013.01); *A61B 5/0071* (2013.01); *G01N 2021/6419* (2013.01); *G01N 2021/6421* (2013.01); *G01N 2021/6441* (2013.01); *G01N 2201/062* (2013.01)

(58) Field of Classification Search
CPC ....... G01N 21/6486; G01N 2021/6419; G01N 2021/6421; G01N 2021/6441; G01N 2201/062; A61B 5/0071
See application file for complete search history.

(56) References Cited

U.S. PATENT DOCUMENTS

| | | | |
|---|---|---|---|
| 2007/0160279 A1* | 7/2007 | Demos | A61B 5/0071 382/133 |
| 2008/0212866 A1* | 9/2008 | Lett | G01N 21/6428 382/133 |
| 2009/0137908 A1 | 5/2009 | Patwardhan | |
| 2009/0224172 A1* | 9/2009 | Scholz | A61B 5/0071 250/459.1 |
| 2010/0134605 A1* | 6/2010 | Demos | A61B 5/0071 348/65 |
| 2010/0254589 A1* | 10/2010 | Gallagher | G06K 9/0014 382/133 |
| 2011/0117025 A1 | 5/2011 | Dacosta et al. | |
| 2011/0224574 A1 | 9/2011 | Sadler et al. | |
| 2012/0053429 A1 | 3/2012 | Trepagnier et al. | |
| 2014/0371582 A1* | 12/2014 | Alfano | A61B 5/0071 600/431 |

OTHER PUBLICATIONS

Bhartia, Rohit, et al. "Label-free bacterial imaging with deep-UV-laser-induced native fluorescence." Applied and environmental microbiology 76.21 (2010): 7231-7237.*
Jamme, Frédéric, et al. "Deep UV autofluorescence microscopy for cell biology and tissue histology." Biology of the Cell 105.7 (2013): 277-288.*
De Jong, Christiaan J., et al. "Deep-UV fluorescence lifetime imaging microscopy." Photonics Research 3.5 (2015): 283-288.*
Fereidouni, Farzad, et al. "Microscopy with UV Surface Excitation (MUSE) for slide-free histology and pathology imaging." SPIE BiOS. International Society for Optics and Photonics, 2015.*
International Search Report and Written Opinion for corresponding International Application No. PCT/US2015/048519 dated Dec. 7, 2015, 9 pages.

* cited by examiner

SYSTEM AND METHOD FOR CONTROLLING DEPTH OF IMAGING IN TISSUES USING FLUORESCENCE MICROSCOPY UNDER ULTRAVIOLET EXCITATION FOLLOWING STAINING WITH FLUORESCING AGENTS

FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

FIELD

The present disclosure relates to systems and methods for structural and molecular imaging of human and animal tissues using fluorescence microscopy under short wavelength, such as ultraviolet light, excitation and more particularly to a system and method which is able to optically section thick tissue samples to obtain high-resolution images of the near-surface tissue microstructure without requiring formalin fixation and paraffin embedding (FFPE) followed by microtome sectioning, or freezing and sectioning of the tissue sample, and which further is able to be used with conventional or novel fluorescing stains and labels, to allow effective analysis of tissue for diagnosis, tissue composition, and/or surgical guidance, such as monitoring surgical margin areas of a biopsy specimen for the presence of tumor cells.

BACKGROUND

The statements in this section merely provide background information related to the present disclosure and may not constitute prior art.

Technology that can provide functional and structural imaging of tissues at a cellular level is of great importance in various fields. Specifically, in the field of clinical practice, histopathologic diagnosis, long considered the gold standard, is based on imaging thin, stained tissue specimens of biopsy or surgical resection, necropsy or autopsy-derived samples, a process that can require hours to multiple days to complete. Ideally, the histologic, genetic or phenotypic information would be attainable in vivo or very quickly after removal of a specimen. We will discuss several potential application areas for a rapid microscopy system, including surgical margin evaluation, biopsy quality control, rapid diagnosis, and rapid molecular characterization. These features are important for clinical pathology applications, but also in the biology, pharmacology and toxicology research settings. Additionally, the tissue sample may still be in-situ in a living organism, as with skin or oral mucosa, as long as it is accessible to appropriate imaging optics.

Surgical margin evaluation: Frozen-section evaluation of biopsies obtained during surgery can be routine part of clinical care but is fraught with difficulties. These include the time involved in orienting, embedding, freezing, cutting, staining, and viewing the resulting stained sections. This process can take 10 minutes or longer per specimen. Moreover, the quality of most of the frozen specimens may be less than optimal, and often lower than that of formalin-fixed paraffin-embedded ("FFPE") specimens. The resulting delays and interpretation challenges limit the use of intra-operative biopsy or surgical margin evaluation. Consequently, if margin assessment is not done intra-operatively, additional surgeries may be required. For example, between 20 and 40% of breast cancer surgeries have to be revisited to remove residual cancer present at or near surgical margins; cancer deposits which ideally would have been detected during the original surgical procedure.

The need for frozen section replacement is well appreciated and many groups and companies have efforts in this area. Techniques include line-scanning confocal systems, wide-field OCT, multi-photon microscopy, as well as other non-imaging based approaches that include light scattering, spectroscopy, electrical impedance, and so on.

Biopsy quality control is another area that the present disclosure aims to address. It is important that biopsies, especially small, relatively non-invasive needle biopsies, contain the tissue of interest. For renal diagnosis, needle biopsies must contain glomeruli; for cancer diagnosis, of course the lesion must be properly sampled, and so on. In the case of samples that have to be partitioned for various purposes—histopathology, flow cytometry, nucleic acid extraction, for example, it is desirable that each aliquot of tissue has the cells or structures of interest. Moreover, it is important in some cases to have an estimate of what percentage of tumor verses stroma may be represented. Having a non-destructive method of rapidly examining the biopsy tissue to ensure that the appropriate content is present would be useful.

Rapid diagnosis of removed tissue samples is also important. Most tissues removed undergo conventional FFPE processing before definitive diagnoses are rendered, incurring delays of days or even weeks, depending on workflow. Having an ability to render diagnoses at the time of biopsy or surgery could decrease delays, diminish patient distress, encourage same-day clinical planning, and decrease overall costs.

Rapid molecular characterization of removed tissue samples is also important. Similarly, many molecular tests, such as immunohistochemistry or immunofluorescence for cancer markers or companion diagnostics are not ordered until after the initial tissue diagnosis, and incur additional days to weeks of delay. Having a microscope system that could provide morphological confirmation along with concurrent or fast but subsequent molecular staining could generate all the necessary tissue-based information on a same-day basis, which could be highly beneficial to the patient, and cost-saving to the provider.

Previous work by Lawrence Livermore National Laboratory and the University of California-Davis resulted in the development of a new imaging method to address these issues including applications in in-vivo imaging. A patent that describes subject matter resulting from this joint work is U.S. Pat. No. 7,945,077 to Demos et al., for "Hyperspectral Microscope for In-vivo Imaging of Microstructures and Cells in Tissues." U.S. Pat. No. 8,320,650 to Demos, assigned to Lawrence Livermore National Security, LLC, and entitled "In-vivo Spectral Micro-Imaging of Tissue," is also related to in-vivo imaging of microstructures and cells in tissues. These two patents are hereby incorporated by reference into the present disclosure. The techniques described in these two U.S. patents enable visualization of the tissue structure and organization at cellular scale in unprocessed tissue specimens. This imaging technology utilizes two physical mechanisms or characteristics. The first is the use of ultraviolet (UV) light that only superficially penetrates tissue. More specifically, the UV light only penetrates tissue on the order of a few micrometers to a few tens of a micrometer, depending on tissue type and wavelength. As a result, the fluorescence signal produced in this superficial tissue layer can be contained within the comparable thickness of the depth of field of the microscope. Oblique angle illumination was also used as means to limit the photon penetration depth for excitation at any given wavelength. The penetration depth can be defined in various ways such as the depth at which the amount of light dose reaching this depth is 1/e (or another predetermined fraction quantity such as 10%) of the incident amount of light.

The second main physical mechanism or characteristic is the use of native fluorophores within the cell compartments of the tissue being analyzed. There is sufficient variability in the concentration of native fluorophores (such as tryptophan, collagen, elastin, NADH) contained within cell compartments providing a natural "staining" method. In addition, images based on the emission of contrast agents can be attained and can be combined with those of native fluorophores to provide additional molecular information.

The methodology of the present disclosure offers several capabilities including: 1) the use of native tissue fluorescing biomolecules and exogenous dyes and labels for image acquisition; 2) short image acquisition times (on the order of milliseconds); and 3) facilitates incorporation into a wide range of instrumentation designs, including hand-held devices. Importantly, the methodology of the present disclosure is considerably less complex and less expensive than prior used technologies. These are significant advantages when compared to other emerging technologies.

In a clinical setting, consequently, there still exists a need for a system and methodology that reduces or eliminates the need for frozen section evaluation of biopsied human and animal tissue. More particularly, there is a need for a system and method which is well suited to intra-operative biopsy and/or surgical margin evaluation of freshly excised tissue samples, without requiring time-consuming and costly freezing and physical sectioning of relatively large tissue samples, and also which is well adapted to be used with conventional fluorescing stains and labels for further aiding evaluation, diagnosis and surgical margin analysis of a tissue sample. In the field of animal research, for basic understanding of body function, for studying the onset and progression of disease, in drug discovery and other areas, there is a need for instrumentation that can provide fast and inexpensive evaluation of a tissue specimen, and that obviates the need to perform conventional time-consuming, technically challenging and relatively expensive histopathology evaluations. The invention discussed here addresses a number of the aforementioned needs.

SUMMARY

In one aspect the present disclosure relates to a method for analyzing tissue. The method may comprise obtaining a tissue sample and exposing the tissue sample to one or more fluorophores including fluorescent dyes or fluorescently labeled molecular probes that preferentially accumulate in tissue or cellular components. An illumination excitation source may be used to illuminate a surface of the tissue sample with one or more ultraviolet (UV) light sources having a wavelength between about 200 nm to about 400 nm. The wavelength may be selected to help limit the penetration of the UV light into the tissue sample to only the approximate selected depth below the surface. A microscope optical system may be used to image the tissue sample. An image acquisition system may be used which receives optical information from the microscope optical system to record one or more images. A display system may be used in communication with the image acquisition system to process and display the image for analysis.

In another aspect the present disclosure relates to a system for analyzing a tissue sample, wherein the tissue sample has been exposed to one or more fluorophores including fluorescent dyes or fluorescently labeled molecular probes that preferentially accumulate in tissue or cellular components. The system may comprise an illumination excitation source configured to illuminate a surface of the tissue sample with ultraviolet (UV) light. The illumination source may have a wavelength selected to help limit the penetration of the UV light into the tissue sample to only an approximate selected depth below the surface. A microscope may be included which provides optical information concerning the tissue sample. An image acquisition system may also be included that produces one or more images from the optical information provided by the microscope. A display system may be included which is in communication with the image acquisition system to process and display the one or more images for analysis.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

2B is a montage of 10×-fields of eosin-stained lamb kidney (same sample as in FIG. 2A) imaged at 10× using a long-working distance lens and an automated x-y-z microscope stage. The individual panels of the composite image were flat-fielded and automatically stitched to create the montage shown. The 3D appearance of the tubules and collecting ducts arise from the fact that they are not exactly co-planar, and the oblique illumination creates shadows which indicate their 3D appearance. Shape-from-shading software, especially with additional excitation angles, can be used to generate 3D quantitative data and possible to highlight or exclude regions above or below a desired image plane.

Figure 3B:
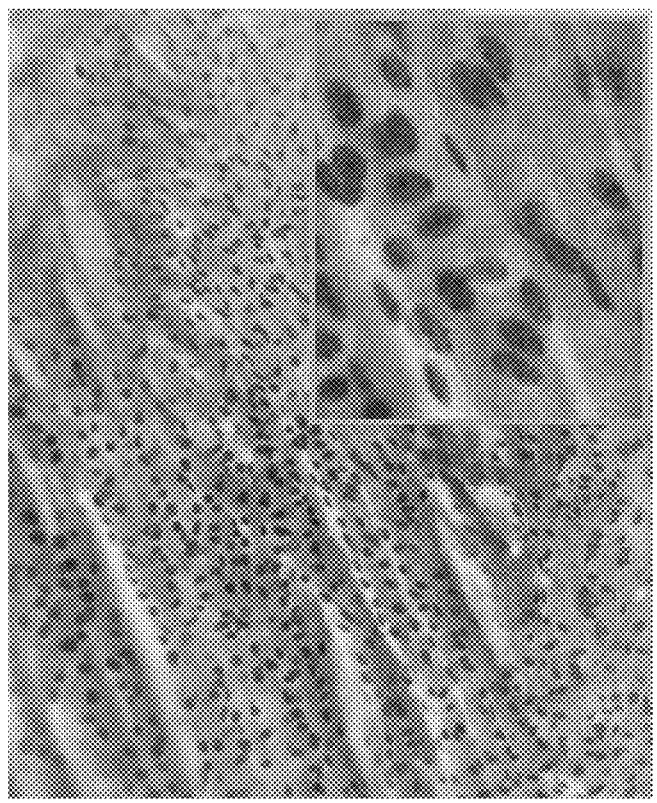
Figure 3A:
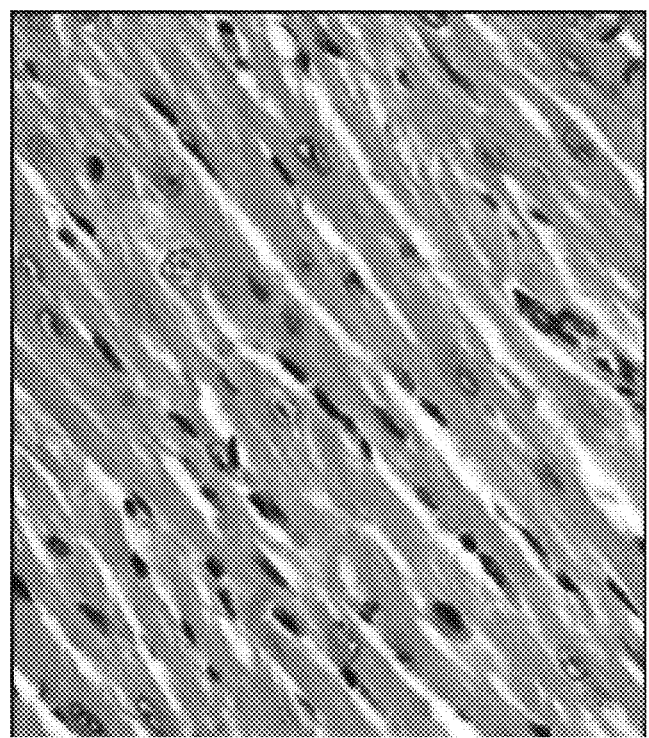

FIG. 3A is an image of conventionally fixed and stained mouse heart muscle, viewed with a standard transmission light microscope. FIG. 3B shows fresh mouse heart muscle tissue stained with both eosin and the nuclear stain, DAPI, and excited with an LED with excitation light centered at 275 nm. The image was taken at 10× magnification with the system depicted, and the eosin and DAPI bands were separately collected using appropriate emission bandpass filters. The resulting images were recolored to simulate traditional bright-field transmission H&E staining. The insert indicates that nuclear features can be visualized.

Figures 4A, 4B:
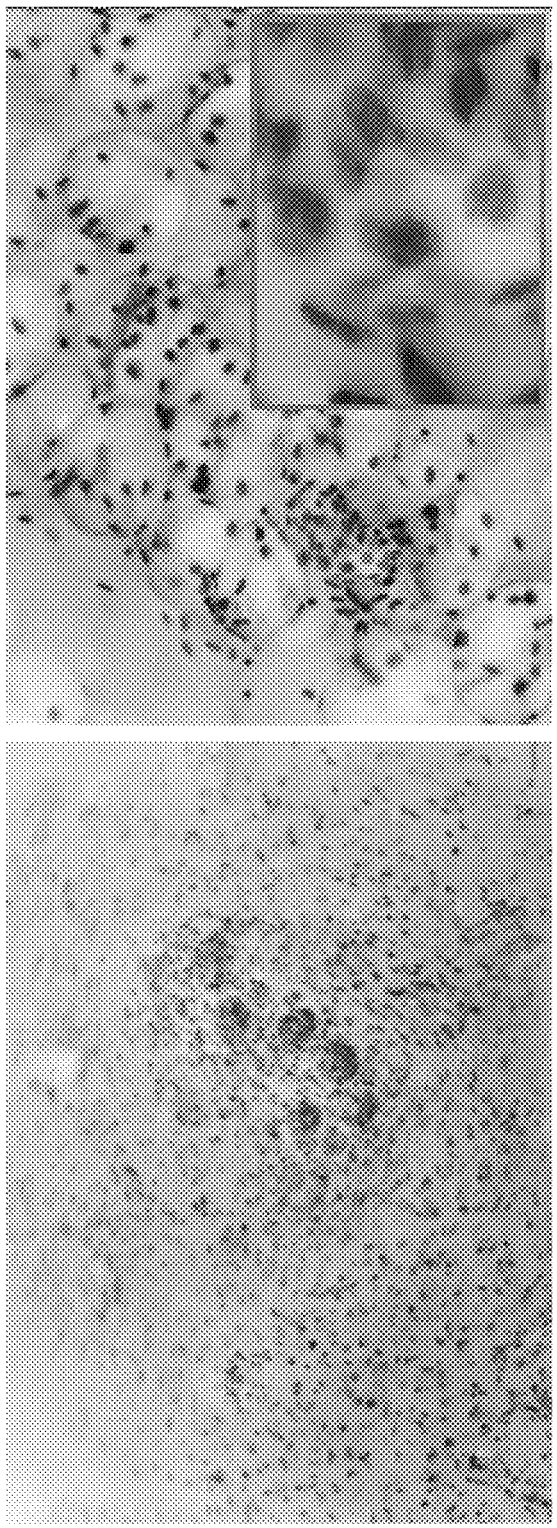

FIG. 4A, shows an image of a normal breast lobule and surrounding tissue stained with eosin and DAPI as above, excited at 275 nm and imaged at low-power (5×). The tissue had been formalin fixed, but was not sectioned, indicating that the method can be applied to fixed as well as fresh tissues. The image was re-colored to simulate standard H&E brightfield staining. FIG. 4B: breast stroma and fat (10×) that was unfixed (fresh), not sectioned, and stained with DAPI and eosin, imaged and recolored to resemble H&E. The insert shows the chromatin texture features that can be observed.

DETAILED DESCRIPTION

The following description is merely exemplary in nature and is not intended to limit the present disclosure, application, or uses. It should be understood that throughout the drawings, corresponding reference numerals indicate like or corresponding parts and features.

With traditional pathology methods, pathology specimens must be physically cut in order to present a thin slice of tissue to a standard microscope. If instead the tissue could be optically sectioned, then freezing, or fixation and paraffin embedding, followed by microtomy, would not be necessary. The previous methods discussed herein, as disclosed in U.S. Pat. Nos. 7,945,077 and 8,320,650 for imaging optically thick specimens inexpensively and efficiently, are centered around oblique wide-field fluorescent imaging of tissue using intrinsic-to-tissue fluorescing biomolecules with short UV light (typically 266 nm) excitation. The present disclosure expands on the teachings of U.S. Pat. Nos. 7,945,077 and 8,320,650 by disclosing new methodologies that make use of fluorescing stains and labels, but still without the need to freeze and physically section large tissue samples. Such stains and labels are widely available and are designed to accumulate in tissue components, cell types, including benign vs. malignant, specific subcellular compartments, and exogenous pathogens, and emit light in different wavelengths so they can be separated during imaging. This particular facet of the methodology of the present disclosure is therefore similar to the FFPE-processed staining of tissue cells in conventional histopathology. However, what is not typically appreciated is that many, possibly most, fluorescent dyes, regardless of emission wavelength range, can be excited in the UV range from 330 nm and below. The present disclosure also expands on the teachings of U.S. Pat. Nos. 7,945,077 and 8,320,650, both incorporated herein by reference, by disclosing new methodologies that allows control of the depth of the section of tissue being imaged as well as techniques that diminish undesirable signal components originating at greater depths.

The methodologies of the present disclosure make possible the evaluation of the cut surface of surgical biopsy material, for example when lightly compressed against a transparent (such as fused-silica or quartz, sapphire, or UV-transmissive plastic) window, with the only tissue preparation being a brief exposure to fluorescent tissue dyes or molecular labels, or other tissue preparation methods such as brief exposure to fixatives such as formaldehyde, paraformaldehyde, various alcohols, acetone, mild detergents and the like to control permeability, pH, osmotic state, ion composition, etc. as needed for optimal tissue labeling. Labeling can be via traditional or non-traditional stains that interact with tissue on a histochemical basis, or can be molecularly specific agents, such as antibodies, aptamers, or nucleic acid probes, and the like, coupled to fluorophores for detection. Interactions with the tissue preparation and labeling reagents can occur over a span of seconds to a few minutes, as only the most superficial few microns of the tissue need to be exposed, and the bulk of the specimen would thus be unaffected.

The fluorescent tissue dyes may comprise, for example, eosin and 4',6-diamidino-2-phenylindole ("DAPI"). The dyes help to provide H&E-like levels of contrast to the surface of the tissue sample being imaged. A set of additional exemplary stains and fluorophores that can be sufficiently excited in the spectral range from 350 nm to 200 nm and that have useful emission bands in the spectral range 350 nm to 950 nm includes but is not limited to the following: Eosin dye family, toluidine blue O, methylene blue, DAPI, Acridine Orange, DRAQ 5, Hoechst 33342 and 33528, calcein-AM, propidium iodide, Nile Blue, Nile Red, Oil Red O, Congo Red, Fast Green FCF, DiI, DiO, DiD and the like, TOTO®, YO-PRO® and the like, Neutral Red, Nuclear Fast Red, Pyronin Y, acid fuchsin, astrazon-family dyes, MitoTracker and other mitochondrial dyes, LysoTracker and other lysosome dyes, safranine dyes, thioflavine dyes, fluorescent phalloidins, plasma membrane stains, such as CellMask™, Evans Blue, SYTOX® Green, and the like, and fluorescent compounds that bind to infectious agents, such as auramine.

In addition, molecular probes can be used, including but not limited to the following: antibodies and related molecules, aptamers, Somamers™, nucleic acid oligomers, LNAs and others. These probes can be directly or indirectly complexed with fluorescent labels, which can include but are not limited to members of the following label classes: Carbon nanotubes, carbon quantum dot, organic fluorescent labels (such as fluorescein, rhodamine, Alexa dyes, Cy2, Cy3, Cy5, Cy5.5 and the like, Texas Red, coumarin-based fluorophores, IRDye 800, indocyanine green, bodipy, DyLight dyes, Oregon Green, phycoerythrin), rare-earth elements, semiconductor quantum dots, organic quantum dots, polymer dots (pDots), fluorescent nanoparticles such as silica beads, polymersomes, porphyrin-based micelles and liposomes, and FRET-based dye conjugates, Alternatively, the fluorescent signals can arise as a consequence of labels administered to a patient or animal model in vivo prior to biopsy, surgery, necropsy or autopsy, and can be detected subsequently using a system 10.

Alternatively, ex-vivo functional labeling can occur if tissue in maintained in a viable state, by incubation, for example, in tissue culture medium, with suitable temperature and oxygenation properties, and exposed to agents that will generate fluorescent labels in cells that actively take them up or appropriately process them. These ex-vivo labeled tissues can then be examined using a system 10.

Figure 1:
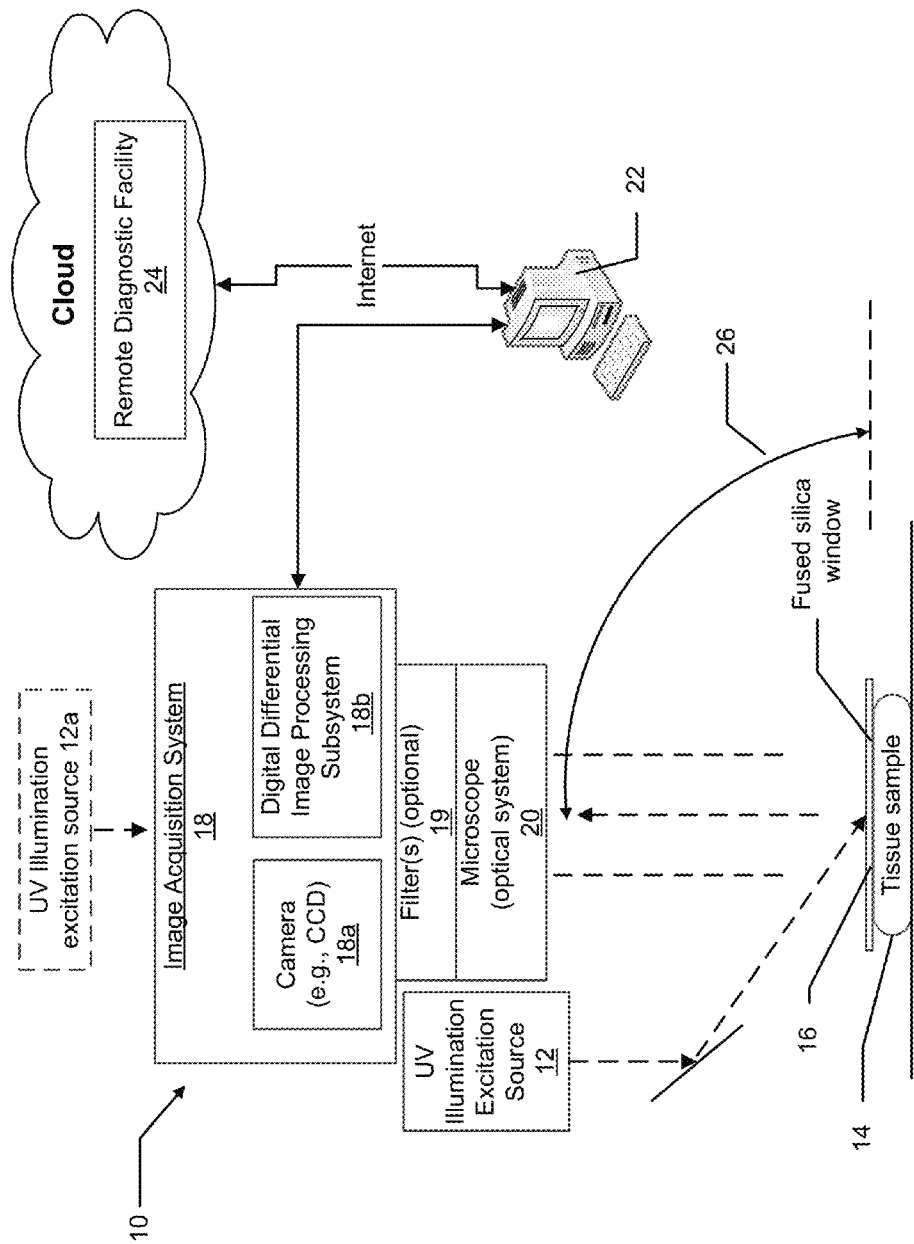
FIG. 1 is a high-level block diagram of one example of a system for implementing a method of the present disclosure.

Referring to FIG. 1, a system 10 in accordance with one embodiment of the present disclosure is shown. The system 10 may be similar to the system described in U.S. Pat. No. 7,945,077, the teachings of which have been incorporated by reference into the present application. The system 10 may incorporate an ultraviolet (UV) illumination source 12 for illuminating a tissue sample 14 with UV light. The UV source 12 may be from a list of sources that include one or more LEDs, lasers, with fixed or tunable emissions, continuum lasers with spectral selection capabilities, conventional or laser-ignited arc lamps, or a krypton-bromine excimer lamp, or other sources with sufficient brightness in the desired spectral range.

The tissue sample may be slightly compressed under or on top of a non- or low-fluorescing window 16 that is transparent to the excitation light, or alternatively imaged directly without the window 16. Additionally, to easily acquire 4 sides of a biopsy specimen, the tissue could be introduced into a potentially disposable rectangular-cross-section cuvette made from UV-transparent plastic. As the tissue is firmly positioned, all four imaging facets should be in direct contact with a conformable tissue surface. To image all 4 faces, the cuvette could be repositioned manually or automatically, or other optical arrangements using mirrors, for example, could be envisioned to permit more than one face to be imaged without sample movement. Other tissue handling methodologies can also be used. At least one imaging camera 18a, in one example a CCD camera, forms a portion of an image acquisition system 18, and acts to record images of the tissue sample 14 which are imaged by a suitable microscope 20 (acting as an optical system). The image acquisition system 18 may also include a digital differential image processing subsystem 18b, which will be discussed further in the following paragraphs.

Because many different fluorescent dyes can be excited by UV light in the 350 to 220 nm range, it is possible to stain with multiple agents at one time (multiplexing). For example, DAPI and eosin can both be present and will generate signals in the blue and green color ranges. Adding another dye or label that emits in the red would provide a third signal, and thus, alternatively, camera 18a may be a color camera capable of capturing the different colors of the generated emission. If additional labels are included, or if better separation of nominal red, green and blue labels is desired than can be achieved by conventional color (RGB) cameras, still further, one or more monochrome cameras or a combination of monochrome and color cameras may be generically represented by camera 18a, and may be used to simultaneously or sequentially acquire images of the tissue sample 14. Optionally, one or more optical filters 19 designed to pass only a predetermined spectrum of emitted light may be incorporated. Such filters 19 may be positioned in conventional filter holders, or deposited over individual pixels in the sensor, or be incorporated in snap-shot imaging systems that employ light-field technology with microlenses, or other single-acquisition designs. Alternatively, tunable filter-based multispectral imaging systems may be employed. More generally, any excitation and/or emission-side system that can generate spectral and spatial information can be used.

The camera 18a transfers image data to the digital differential image processing subsystem 18b, for processing, if necessary, and the resulting images are delivered to the display system 22. After color or spectral unmixing, or other processing, individual component images corresponding to different label distribution and abundance patterns can be generated. Alternatively, a fused single image containing combined dye or fluorophore information can be generated, and rendered, with real or pseudocoloration. In this example the display system 22 is formed by a desktop computer system with a monitor, although the display system 22 may just as well be a laptop computer, an electronic tablet, a smartphone or any other device capable of displaying a digital image. The images obtained may also be transmitted from the display system 22 to a remote facility 24 for examination. Alternatively, the image may be transmitted from the system 10 directly (i.e., bypassing the display system 22) to the remote facility 24. In either event, the images obtained may be examined virtually immediately by trained personnel after acquisition using the native tissue fluorescence and/or after the tissue has been exposed to selected fluorescing dyes or molecular labels. The obtained image(s) may also be saved to a suitable storage system of the display system 22 and/or to a remote digital media storage subsystem. Additionally, as described briefly below, the images can also be interpreted or quantitated using automated or semi-automated computer programs.

A particular advantage of the system 10 and methodology of the present disclosure is that light at the wavelengths described herein is strongly absorbed by tissue components such as proteins and nucleic acids. As a result a majority of the excitation light only penetrates below the surface of a tissue sample to a level of just one or a few cells deep. This obviates the need for physical sectioning. Another significant advantage is that virtually all fluorescent dyes can be excited by light in the UV spectral region employed by the methodology of the present disclosure. This significantly simplifies the use of multiple fluorescent contrast agents, including molecular probes.

Another advantage is that the illumination is oblique, rather than on-axis, and provides shading or shadowing information that provides some 3-dimensional information. This optical effect is evident in directly acquired images to generate perceptible shape or depth sensations, or can be input into various mathematical algorithms, for example, tomography, for creating computationally acquired depth information or additional axial sectioning, or other resolution enhancements.

The use of fluorescing stains and probes in combination with a methodology that does not require freezing and physical sectioning of tissue samples enables rapid imaging, typically enabling a wide-field-of-view and high-resolution image to be built up in a minute or less. In addition, staining of the tissue with directly labeled antibodies or nucleic acid probes (which can be rapidly hybridized, such as with RNA fluorescence in situ hybridization ("Turbo RNA FISH.") will also be possible, and specific and non-specific staining could be readily distinguished by using a targeted and non-targeted probe simultaneously. With care and suitable optical and post-processing maneuvers, pathologist-acceptable image quality is achievable. The image quality may even be suitable for primary diagnosis work. The system 10 and methodology of the present application is low in cost compared with other approaches as described above. This is in part because no lasers, or even dichroic mirrors, are required for implementing the methodology. Because UV light in this range is not transmitted by conventional microscope optics, no excitation-blocking filters are required. In one instance the methodology of the present disclosure may be implemented using only one or more UV-LED illumination sources, a microscope lens, a suitable color camera, and a suitable display/computing system. With suitable optomechanics, it is evident that a cell-phone camera could also provide a useful sensor and could be integrated into a low-cost, field-deployable system.

This system 10 and method of the present disclosure further teaches how to optimize imaging of tissue specimens using widely available contrast agents so that high quality scans of extended specimens can be obtained in a shorter period of time than what would otherwise be possible with conventional methods that involve freezing and physical sectioning of tissue samples. There are multiple technical considerations that should be taken into account when implementing the teachings of the present disclosure. These include, but are not limited to: a) selection and/or discovery of suitably optimized contrast agents and staining methods; b) methods to minimize cost of instrumentation; c) methods to minimize the time required for imaging of large specimens; d) selection of instrumentation and configurations to perform specific tasks; e) image storing, transmission and processing; and f) methods to control the imaging depth. Each of the above considerations will be discussed next as it relates to the present invention in the same order as presented above.

A) Selection and/or Discovery of Suitably Optimized Contrast Agents

The contrast agent used should be able to provide staining of subcellular and intracellular compartments of fresh tissue specimens (with or without brief exposure to conditioning solutions that optimize staining, by for example, changing the pH, ionic strength, permeability of cells and subcellular structures, hydration state, solvent, protein and nucleic acid structure and cross-linking, antigen availability, and the like, to enable visualization of tissue microstructure and organization suitable for histopathologic diagnosis or characterization. The contrast agents should absorb in the UV spectral range used for excitation and emit at a longer wavelength such as in the visible spectrum. The contrast agents should stain the tissue upon physical exposure as fast as possible to minimize the processing time. The contrast agent should not substantially alter or damage the macro- or microstructure of the tissue. The time of exposure of the tissue to the solution containing the contrast agent may be optimized.

The contrast agent may include components that fix or precipitate proteins, and that permeabilize cells, such as alcohols, detergents or formaldehyde. These may require just seconds for action as only the top few microns of tissue have to be affected. Selected contrast agent(s), in conjunction with the imaging technology and suitable post-processing, can generate H&E-like images that resemble current diagnostic images and that meet subjective quality standards, as adjudicated by practicing surgical pathologists. However, the resulting images, even if they have optically high quality, may be dissimilar to those obtained with frozen section or FFPE techniques, as the familiar artifacts (retraction, nuclear clearing and chromatin clumping, e.g.) of these methods may be absent in unfrozen, unfixed, and non-paraffin-embedded specimens. Additionally, methods to optimize binding and detection of molecular probes will be necessary for visualization of antigens, genes, or expressed RNA molecules. There are rapid techniques using direct-labeled antibodies that allow for rapid detection of HER2 protein, for example, or of various RNA molecules via TURBO FISH, and the like.

B) Methods to Minimize Cost of Instrumentation

The cost of instrumentation is directly related to the imaging and processing methods, but also to the quality of the images captured and the volume of information required for diagnosis. Within a certain set of these operating parameters, suitable instrumentation can be selected to minimize the cost. Such cost will be dependent on the cost of acquisition of the optical elements including microscope objectives and filters, the cost of the light sources and the cost of the cameras/detectors. Depending on the availability and cost of these components, specific instrumentation architecture can be designed. Specifically, a single monochrome camera can be used to acquire multiple spectral images but this will cause a longer time to scan large specimens. On the other hand, multiple cameras can be used in conjunction with bright light sources to minimize the time to scan large specimens, but this will increase the cost of instrumentation. Alternatively, if resolution and light-intensities are sufficient, even a consumer-grade RGB camera may be suitable. This could allow full-color imaging capturing of the emission of different fluorescing components (intrinsic or extrinsic) with a single exposure. Alternatively, snap-shot spectral cameras, such as those that use filtered pixel masks or light-field imaging with lenslet arrays and configurable filter inserts can generate multiple wavelength images in a single exposure.

Figure 2A:
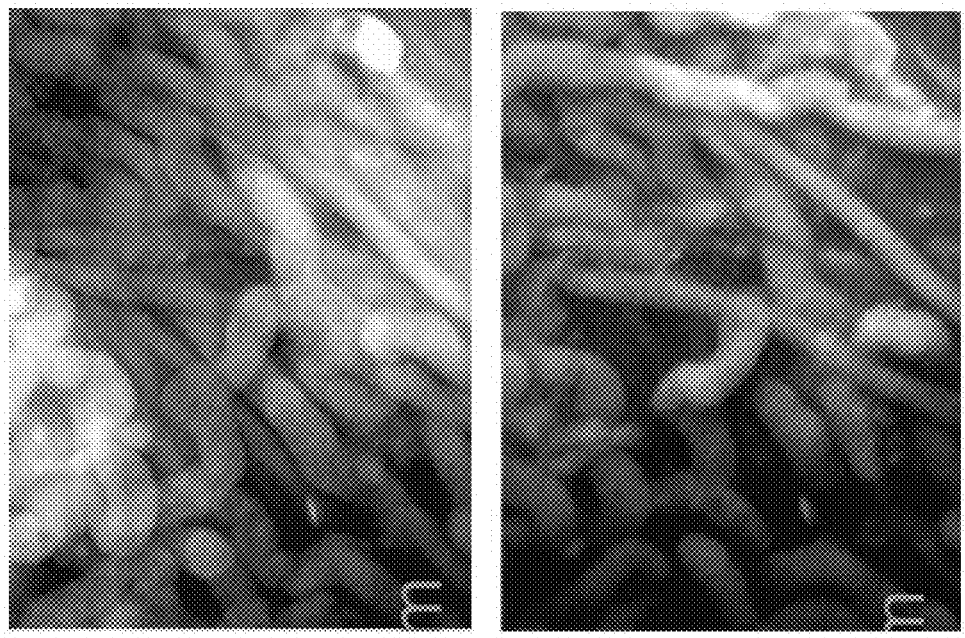
FIG. 2A is a pair of images of the same field of unfixed lamb kidney briefly exposed to a standard ready-to-use histology eosin solution, and excited at 405 nm (blue light, visible range) and also at 275 nm (UV), and imaged using the microscope system depicted in FIG. 1. The 405-nm excitation light penetrated an estimated several 10's of microns into the tissue, and caused emission from multiple cell layers. The 275-nm excitation light penetrated much less deeply, and allowed the discrimination of tubules lying closest to the surface of the tissue.
Figure 2B:
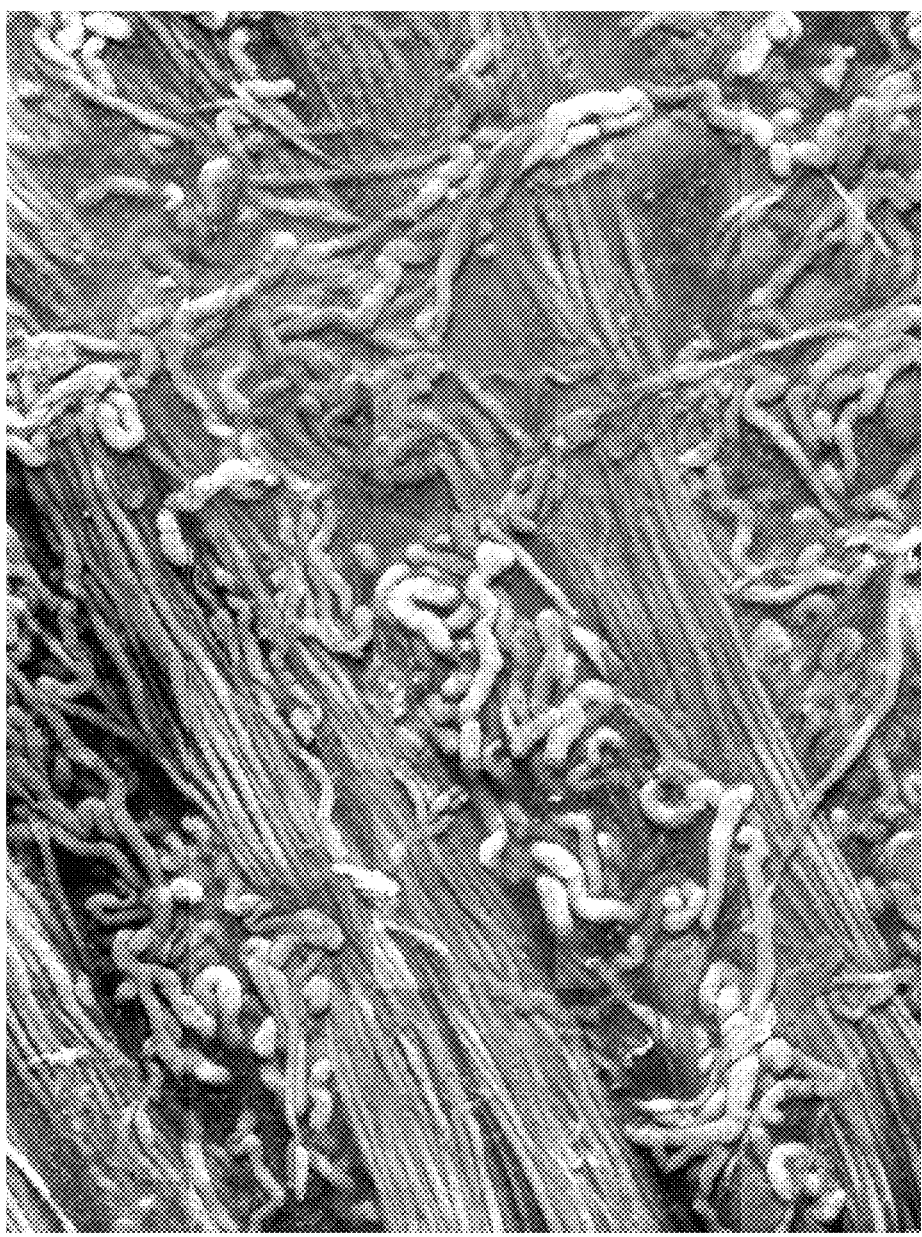

A large specimen can be imaged with this general approach using various methods such as: a) stitching high-resolution area-illuminated images of smaller sections, as shown in FIG. 2B; b) scanning UV light point-by-point using a scanning method; or c) using a line of UV light for line-scanning. Compressive sensing using, for example, structured illumination and single-pixel detectors may also be suitable. Alternatively, methods that can maintain resolution while viewing large fields-of-view can be employed, such as high-NA low-power lenses, high-pixel count cameras, and computational approaches that use information from multiple images to generate high-quality renderings. Sample movement, if necessary, can be facilitated by attaching the sample holder module of the detector assembly to a motorized stage, or the sample or stage can be moved manually and the resulting images can be stitched together automatically. Selection of the proper instrumentation will thus be based on a variety of technical specifications, as well as the cost of acquisition of the parts at the time of assembly.

C) Methods to Minimize the Time Required for Scanning of Large Specimens

The scanning time depends on a number of parameters related to the instrumentation such as the sensitivity of the detection system, the numerical aperture of the lens system, the transmission efficiency of any filters, the excitation intensity, the quantum efficiency of the cameras and/or detectors and concentration of the contrast agents. There are also limiting factors such as the maximum excitation intensity before photo-bleaching of the contrast agent, or actual tissue photodamage or tissue ablation.

The required spatial resolution plays a key role in the scanning speed. The signal-to-noise ratio during image acquisition should remain sufficiently high so that image quality is not impaired. As multiple images of different emission bands of each site may be needed, using multiple cameras or other methods for parallel image acquisition will enable faster scanning speeds. Alternatively, a standard full-color (RGB) sensor may also be used to decrease the number of exposures required, or various techniques for snap-shot multispectral imaging can be employed.

D) Selection of Instrumentation and Configurations to Perform Specific Tasks

The discussion above under sections A, B and C regarding various technical considerations highlights the various possible configurations and types of instruments that may be used to implement the teachings of the present system and method. These are related to the image capturing apparatus and scanning speed and methods. Another aspect arises from the illumination geometry that will be discussed in technical consideration F), below. Overall, the imaging methodology requires apparatus for illumination, light collection and filtering, image acquisition, scanning large specimens, creating composite digital images and image analysis and enhancement. Particularly low-cost implementations can be designed for use in resource-poor settings relevant to global health applications, leveraging cell-phone or similar sensors and computing and communication platforms.

E) Image Storing, Transmission and Processing

The images of the samples may be digitized immediately and saved on various types of digital storage media types. The image files can be transmitted immediately using current and future information technologies so that tele-consultation can be facilitated. The addition of machine-learning (or other modality) image segmentation, classification, and quantitation capabilities may increase performance and utility of the present system and method and may help to lead to automated diagnosis.

F) Methods to Control the Imaging Depth

Controlling the imaging depth is of particular importance in order to produce images with suitable quality for diagnostic analysis. The imaging depth in current histopathology analysis is controlled by cutting thin sections of processed tissues before staining and viewing under a microscope. With the present system and method, the sectioning is accomplished optically, rather than by physical slicing of the tissue sample, although the sample may have to be cut in such a way that a flat surface can be apposed to a clear optical sample support to provide high-quality images. The sample support surface, as with a conventional coverslip, must have the appropriate thickness and refractive index to provide optimal image quality. Optically controlling the penetration depth of the excitation photons from the illumination source 12 into the tissue sample 14 is a significant feature of the system 10. The optimal penetration depth may vary somewhat, but at the present time one preferred penetration depth is about 5-25 micrometers, and more preferably about 10 micrometers. This depth represents the distance from the surface of the tissue sample 14 that will cause attenuation of the illumination by a certain fraction. However, there will be some photons that can reach deeper than this depth, and as such these deeper penetrating photons will provide a signal which is outside of the intended imaging zone (i.e., the zone between the surface and about 10 micrometers below the surface). It may be useful to exclude the fluorescence signal generated by such photons from layers deeper than the chosen imaging depth.

There is also another mechanism that can cause a similar effect for the application discussed in the present application, which is namely the use of fluorescing contrast agents to highlight specific tissue components or molecular targets. Specifically, the excitation of the tissue with UV light generates autofluorescence in the near-UV. The fluorescing contrast agents can be excited by both the UV excitation and the near-UV autofluorescence. The near-UV autofluorescence will be generated inside the tissue and will be directed equally in all directions, thus causing some additional excitation, and thus emission arising from deeper into the tissue.

The system and method of the present disclosure addresses all of the aforementioned considerations. For simplicity, the following discussion will be separated into two main issues: A) control of the depth of the imaging zone, and B) removal of unwanted signal components via image processing.

The depth of the imaging zone can be controlled using the excitation wavelength of the signal from the UV illumination excitation source 12. This imaging method involves using UV excitation to provide shallow penetration depth. But if the exact depth of the imaging zone must be controlled, the excitation wavelength must be precisely tuned to the proper wavelength. The depth of the imaging zone is generally decreasing or remains approximately the same as the wavelength of the excitation light is tuned to shorter values. This is true from about 370 nm down to about 240 nm. Below about 240 nm there is a sharp decrease of the penetration depth as the wavelength is further decreased. Therefore, it is possible to choose the proper excitation wavelength in order to achieve a predetermined penetration depth. This is illustrated in FIG. 2A.

Another parameter that can be used to control the depth of the imaging zone is the incidence angle of the excitation. Normal incidence, that is, arranging the UV illumination excitation source 12 at an angle 26 of about 90 degrees to a plane in accordance with the imaged surface of the tissue sample 14, provides deeper penetration than oblique incidence. This arrangement is shown with illumination excitation source 12a shown in FIG. 1. In this instance the excitation light may be passed through the objective of the imaging device (e.g., microscope 20) to illuminate the tissue sample 14 at 90 degrees with respect to the surface of the tissue sample. With the illumination excitation source arranged at an oblique angle to the upper surface of the tissue sample 14, as indicated by illumination excitation source 12 in FIG. 1, the penetration depth will be less than it would be with the illumination excitation source 12 arranged at 90 degrees relative to the surface of the tissue sample 14. The penetration depth decreases as the incidence angle 26 increases (i.e., moves towards 90 degrees relative to the surface of the tissue sample 14). By carefully controlling the incidence angle 26, one can select a relatively precise penetration depth for the UV light into the tissue sample 14.

Image processing can also be used to remove unwanted image components. Such components may be the out-of-focus and/or out-of-the-imaging zone image components. To remove these unwanted components, differential imaging methods implemented via a suitable digital differential image processing subsystem 22a (FIG. 1) can be employed. The term "differential" is used as a generic term to describe one or more imaging operations that may be performed by the subsystem 22a that enhances certain signal components, while it suppresses unwanted signal components. Such operation may involve, but is not limited to, image subtraction, image division or other types of mathematical image processing via pixel-by-pixel operations or other means.

Image processing of this type requires at least two images containing different relative contributions of the in focus signal versus the unwanted signal components. There are multiple different methods that can be employed that will be listed next but other methods that present the same logic may be formulated that are similar to those described therein.

These two or more images may be obtained using:

1) two or more excitation wavelengths or spectral bands using the same emission spectral band for imaging;

2) two or more different emission wavelengths or spectral bands using the same excitation wavelength 3) two or more excitation wavelengths or spectral bands and two or more different emission spectral bands for imaging;

4) two or more light excitation incident angles using the same excitation wavelength or spectral band;

5) two or more light excitation incident angles using different excitation wavelengths or spectral bands;

6) two or more light excitation incident angles using the same emission spectral band for imaging;

7) two or more light excitation incident angles using different emission spectral bands for imaging;

8) two or more polarization states for excitation using the same polarization state of emission used for imaging;

9) a single polarization state for excitation using different polarization states of emission for imaging;

An array of images captured using various incident angles and/or various rotational angles of the excitation light designed to provide images that can be used, via image processing and/or mathematical reconstruction, to exclude deeper or superficial signals, as desired.

10) Additional combination of the above;

11) Two or more images acquired using varying spatially modulated illumination (excitation) patterns;

12) An array of images captured using various spatially modulated illumination (excitation) configurations designed to provide images that can be used, via image processing and/or mathematical reconstruction, to exclude deeper or superficial signals, as desired.

13) An array of images with the microscope system focused in different depths above and below the tissue surface can be used via image processing and/or mathematical reconstruction, to exclude deeper or superficial signals, as desired.

Additional information from the images can be obtained using multiple oblique illumination sources arranged radially around the optical axis, including shape-from-shading analysis, as suggested by the image shown in FIG. 2B.

Referring to FIG. 3, images of mouse heart tissue are shown. In FIG. 3A, the dark blue round features represent the nuclei and pink color represents the cytoplasm containing cardiac muscle contractile elements. The image of FIG. 3A is a photograph of a standard histological section of formalin-fixed FFPE-processed hematoxylin and eosin stain (H&E stain) tissue. This represents the well-known and presently most widely used manner of mechanically sectioning and staining a tissue specimen for medical diagnosis purposes. This well-known process requires about 24 hours processing and handling time (with typical histology lab workflow) before the tissue sample can be viewed with a microscope by a pathologist. The image of a tissue specimen shown in FIG. 3B was obtained using the system 10 and method of the present disclosure in conjunction with fluorescing stains and labels. The tissue specimen of FIG. 3A was immersed in a solution containing eosin and DAPI for 30 seconds. Two fluorescence images were then acquired by a microscope (e.g., lens subsystem 20 in FIG. 1) using filters centered at 450 nm and 550 nm to selectively map the localization of DAPI (which binds to nuclear proteins) and eosin, respectively. Commercially available software was used to create the composite image (FIG. 3B) that simulates the H&E-appearance of conventional histopathology. The image of FIG. 3B was acquired in about one minute—including the staining of the tissue specimen. Since the image of FIG. 3B is a digital image, it can be transmitted immediately via wired or wireless digital transmission subsystems to a remote diagnostic facility or hospital. If a wireless communication link is employed, the images could be relayed virtually immediately to a pathologist located anywhere in the world. In addition, the tissue specimen remains intact, apart from superficial staining or other surface modifications from brief exposure to various solutions because no physical sectioning apart from possible bisecting to provide a flat face for imaging is required for the analysis to be performed.

In FIG. 3B a larger concentration of nuclei 102 are visible in the image due to imaging a thicker tissue section. Whereas FIG. 3A shows an image of about a 5-μm thick section of the tissue specimen, the image of FIG. 3B is obtained from about a 20-μm imaging depth of the top layer of the tissue specimen. With improved optical sectioning, for example using shorter wavelength illumination, the present system 10 and method can generate images that are qualitatively similar to those generated using conventional histopathology methodologies for rapid tissue assessment. It is important to note that conventional methodologies using frozen section protocols typically provide lower quality images due to freezing artifacts and other issues, take about 10-20 minutes to accomplish, and physically compromise the examined tissue specimen.

FIGS. 4A and 4B show additional images of tissue samples obtained using the present system and method. FIG. 4A shows a breast lobule and surrounding tissue (5× magnification). The tissue had previously been formalin-fixed but had not been sectioned. FIG. 4B shows breast stroma (mostly fat) (10× magnification unfixed (fresh), not sectioned. The tissue of FIG. 4B was stained with DAPI and eosin, imaged and recolored to resemble H&E. The insert illustration in FIG. 4B indicates that fine chromatin texture features can be observed. The appearance is different from frozen section or standard FFPE slides as intact fat globules are still present.

The present system and method thus enables much more rapid analysis and evaluation of tissue specimens in way that has limited impact on the integrity of the tissue specimen, which can be available for downstream processing, including standard FFPE-based histology, extraction of genetic material or other procedures.

While various embodiments have been described, those skilled in the art will recognize modifications or variations which might be made without departing from the present disclosure. The examples illustrate the various embodiments and are not intended to limit the present disclosure. Therefore, the description and claims should be interpreted liberally with only such limitation as is necessary in view of the pertinent prior art.

G) Methods of Handling the Specimen for Image Acquisition

For imaging within the teachings of this invention, it is strongly preferred that a relatively flat surface of the sample be presented to the microscope system. The flat surface can be achieved via various means. These included but not limited to the following: a) the surface may be naturally flat; b) the sample is attached to a holder that incorporates ability to rotate and translate the sample in multiple orientations so that each imaged sub-section of the sample can be presented for image acquisition in a flat (compared to the image plane) orientation; c) The specimen is brought in contact with flat optical surface that allows penetration of the excitation and transmission of the generated signal for image acquisition but it applies sufficient pressure (due to either its own weight, the sample's weight or with the application of an additional external weight or pressure) to generate a flat surface; d) the sample is inserted inside a suitable container that encompasses flat or potentially curved surfaces (such as a cuvette) that allows penetration of the excitation and transmission of the generated signal for image acquisition in order to present multiple flat surfaces of the specimen covering nearly all exposed surface of the specimen.

The sample support material to generate the flat surface(s) is an ultraviolet-transmissive material that can include quartz, fused silica, sapphire, or a UV-transmissive plastic, such as TPX® polymethylpentene. The specimen is translated and/or rotated with respect to the image plane of the microscope so that a sequence of images of the specimen can be acquired with adequate spatial and spectral resolution. Subsequently, the images can be stacked together (image stitching) to provide a high-resolution image of the entire specimen or a section of the specimen as needed.

What is claimed is:

1. A method for analyzing tissue comprising:
   obtaining a tissue sample;
   exposing the tissue sample to one or more different exogenous fluorophores excitable in a range of about 300 nm to about 200 nm and having a useful emission band from about 350 nm to about 900 nm, and including one or more fluorescent dyes or fluorescently labeled molecular probes that accumulate in tissue or cellular components;

exciting, with an ultraviolet (UV) light source, the one or more different exogenous fluorophores with a first wavelength of UV light between about 200 nm and about 290 nm;

collecting with an optical system, emissions from each of the one or more different exogenous fluorophores at a second wavelength different from the first wavelength of UV light, being from about 350 nm to about 950 nm, and being generated in response to the first wavelength of UV light.

2. The method of claim 1, wherein the UV source comprises at least one of:
an LED;
a laser;
a tunable laser; or
a continuous source including at least one of a continuum laser light source, an arc-lamp, a laser-ignited arc lamp, or a krypton-bromine excimer lamp.

3. The method of claim 1, wherein the tissue is supported by a support formed by an ultraviolet-transmissive material that includes at least one of include quartz, fused silica, sapphire, or a UV-transmissive plastic, including TPX® polymethylpentene, such that at least one of:
the support is configured as a planar window against which the tissue sample is pressed to ensure desired optical properties at interface between the planar window and the tissue sample; or
the support is configured as a cuvette-shaped object, and disposable, into which the tissue is introduced, and provides four or more flat or curved surfaces for circumferential imaging.

4. The method of claim 1, wherein the one or more fluorescent dyes or fluorescently labeled molecular probes are selected to enhance a contrast of tissue or cell components when viewed under a microscope, and comprised of at least one of:
Nucleus;
cytoplasm;
cellular membranes; and
mitochondria.

5. The method of claim 1, wherein the one or more fluorescent dyes or fluorescently labeled molecular probes are selected to enhance a contrast of tissue or cell components viewed under a microscope, and are comprised of at least one of:
subcellular organelles;
lipids;
extracellular tissue constituents including at least one of connective tissue including collagen and extracellular matrix;
cyst contents;
foreign bodies;
infectious agents;
pigments;
exogenous marking dyes for orientation;
in a case of molecular probes:
proteins;
post-translational modifications;
DNA or RNA sequences including genes, chromosomal regions or DNA constituents;
RNA transcripts, coding and non-coding; and
lipid rafts.

6. The method of claim 1, in which the one or more different exogenous fluorophores include histological or histochemical fluorescent dyes and include at least one of: Eosin dye family, toluidine blue O, methylene blue, DAPI, Acridine Orange, DRAQ 5, Hoechst 33342 and 33528, calcein-AM, propidium iodide, Nile Blue, Nile Red, Oil Red O, Congo Red, Fast Green FCF, DiI, DiO, DID, TOTO® dye, YO-PRO® dye, Neutral Red, Nuclear Fast Red, Pyronin Y, acid fuchsin, astrazon-family dyes, MitoTracker dye, mitochondrial dyes, LysoTracker dye, lysosome dye, safranine dyes, thioflavine dyes, fluorescent phalloidins, plasma membrane stains, fluorescent compounds that bind to infectious agents.

7. The method of claim 1, wherein molecular probes including antibodies and molecules, aptamers, nucleic acid oligomers, a LNAs LNA molecular probe, are directly or indirectly complexed with fluorescent labels, and wherein the fluorescent labels include members of at least one of the following label classes: Carbon nanotubes, carbon quantum dot, organic fluorescent labels including fluorescein, rhodamine, Alexa dyes, Cy2, Cy3, Cy5, Cy5.5 dyes, Texas Red dye, coumarin-based fluorophores, IRDye 800 dye, indocyanine green dye, bodipy dye, DyLight dyes, Oregon Green dye, phycoerythrin dye, rare-earth elements, semiconductor quantum dots, organic quantum dots, polymer dots (pDots), fluorescent nanoparticles including silica beads, polymersomes, porphyrin-based micelles and liposomes and dye conjugates.

8. The method of claim 1, wherein the one or more different exogenous fluorophores are coupled to molecular probes that bind to specific molecules within extracellular components, cells or subcellular components, or are taken up or differentially processed by different cell types relative to normal epithelium or stroma, or infectious agents, and wherein:
a labeling process occurs (in vivo) in a patient prior to tissue excision, if the patient is administered one or more fluorescent compound with desired tissue or cellular specificity;
a labeling process occurs after tissue excision or sampling, during ex-vivo short-term culture under conditions that can support cellular viability, including maintenance in oxygenated, warmed tissue culture media; or
a labeling process occurs in cells or tissues under conditions that do not require viability, including exposure to probes under immunofluorescence or in-situ hybridization conditions.

9. The method of claim 1, further comprising using an image acquisition system that operates as at least one of:
a two-dimensional area-sensor or a camera or the like to record at least one image from a region of a tissue sample using fluorescence of native tissue molecules or a florescence of a contrast agent; or
a point-detector that scans a section of the tissue sample point-by-point to generate at least one image from a region of a tissue sample using fluorescence of native tissue molecules or florescence of a contrast agent; or
a line-detector that scans a section of the tissue sample line by line to generate at least one image from a section of the tissue sample using fluorescence of native tissue molecules or florescence of a contrast agent.

10. The method of claim 9, wherein using the image acquisition system comprises supplying a plurality of images obtained from different sections of the tissue sample for subsequent stitching together to form a single enlarged image of a larger section of the tissue sample of an entirety of the tissue sample.

11. The method of claim 1, wherein a penetration depth of the first wavelength of UV light into the tissue sample is controlled in part by positioning the illumination excitation source at a desired incidence angle relative to the surface of the tissue sample and in part by adjusting the first wavelength of UV light.

12. The method of claim 1, wherein an incidence angle is between 40 and 80 degrees relative to the surface of the tissue sample.

13. The method of claim 11, wherein the incidence angle is 90 degrees or less, relative to the surface of the tissue sample.

14. The method of claim 1, wherein a penetration depth of the first wavelength of UV light below the surface of the tissue sample is between 5 micrometers to 25 micrometers.

15. The method of claim 14, wherein the penetration depth is 10 micrometers.

16. The method of claim 9, wherein the using the image acquisition system includes acquiring a plurality of images containing different relative contributions of an in-focus signal versus unwanted signal components.

17. The method of claim 16, wherein acquiring a plurality of images comprises at least one of:
a) acquiring images using two or more excitation wavelengths and a single emission spectral band for imaging;
b) acquiring two or more different emission spectral bands using the same excitation wavelength or spectral bands;
c) acquiring images using two or more excitation wavelengths and two or more different emission spectral bands for imaging;
d) acquiring images using two or more light excitation incident angles using the same excitation wavelength;
e) acquiring images using two or more light excitation incident angles using different excitation wavelengths;
f) acquiring images using two or more light excitation incident angles using the same emission spectral band for imaging;
g) acquiring images using two or more light excitation incident angles using different emission spectral band for imaging;
h) acquiring images using two or more polarization states for excitation using the same polarization state of emission used for imaging;
i) acquiring a single polarization state for excitation using different polarization states of emission for imaging;
j) acquiring images using two or more light excitation rotational angles at a specific incident angle using different emission spectral band for imaging;
k) using combinations of a) through j);
l) acquiring two or more images using varying spatially modulated illumination (excitation) patterns; and
m) acquiring an array of images using different spatially modulated illumination (excitation) configurations designed to provide images that are used, via image processing, to exclude deeper or superficial signals.

18. A system for analyzing a tissue sample, wherein the tissue sample has been exposed to one or more exogenous fluorophores excitable in a range of about 300 nm to about 200 nm and having a useful emission band from about 350 nm to about 900 nm, and including fluorescent dyes or fluorescently labeled molecular probes, that accumulate in tissue or cellular components, the system comprising:

an illumination excitation source configured to illuminate a surface of the tissue sample with an ultraviolet (UV) light to excite the one or more different exogenous fluorophores with a first wavelength of UV light between 200 nm and 290 nm;
a microscope which provides optical information concerning the tissue sample, the microscope collecting emissions from each of the one or more different exogenous fluorophores at a second wavelength different from the first wavelength of UV light, the second wavelength being from 350 nm to 950 nm, and being generated in response to the first wavelength of UV light; and
an image acquisition system that produces one or more images from the optical information provided by the microscope.

19. The system of claim 18, wherein the illumination excitation source comprises at least one of:
an LED;
a laser;
a tunable laser; or
a continuous source including at least one of a continuum laser light source, an arc-lamp, a laser-ignited arc lamp, or a krypton-bromine excimer lamp.

20. The system of claim 18, wherein the tissue sample is supported by a support formed from an ultraviolet-transmissive material that includes at least one of quartz, fused silica, sapphire, or a UV-transmissive plastic including TPX® polymethylpentene, such that at least one of:
the support can be configured as a planar window against which the tissue sample is pressed to ensure desired optical properties at an interface with the planar window; or
the support is configured as a cuvette-shaped object, which is disposable, into which the tissue is introduced, and provides four or more flat surfaces or curved surfaces for circumferential imaging.

21. The system of claim 18, wherein the image acquisition system is configured to acquire a plurality of images containing different relative contributions of an in-focus signal versus unwanted signal components, and wherein the plurality of images comprise at least one of:
a) images using two or more excitation wavelengths and a single emission spectral band for imaging;
b) two or more different emission spectral bands using the same excitation wavelength or spectral bands;
c) images using two or more excitation wavelengths and two or more different emission spectral bands for imaging;
d) images using two or more light excitation incident angles using the same excitation wavelength;
e) images using two or more light excitation incident angles using different excitation wavelengths;
f) images using two or more light excitation incident angles using the same emission spectral band for imaging;
g) images using two or more light excitation incident angles using different emission spectral band for imaging;
h) images using two or more polarization states for excitation using the same polarization state of emission used for imaging;
i) a single polarization state for excitation using different polarization states of emission for imaging;
j) images using two or more light excitation rotational angles at a specific incident angle using different emission spectral band for imaging;

k) using combinations of a) through j);
l) two or more images using varying spatially modulated illumination patterns; and
m) an array of images using different spatially modulated illumination configurations that provide images that are used, via image processing, to exclude deeper or superficial signals.

* * * * *